United States Patent [19]
Vines et al.

[11] Patent Number: 5,493,926
[45] Date of Patent: Feb. 27, 1996

[54] METHOD OF IDENTIFYING A WEAKEST INTERFACE WHERE DELAMINATION IS MOST LIKELY TO OCCUR IN A MULTI-LAYER DIELECTRIC FILM STACK

[75] Inventors: Landon B. Vines, San Antonio, Tex.; Felix H. Fujishiro, San Jose, Calif.; Danny W. Echtle, San Antonio; Annette Garcia, Pleasanton, both of Tex.

[73] Assignee: VLSI Technology, Inc., San Jose, Calif.

[21] Appl. No.: 408,652

[22] Filed: Mar. 21, 1995

[51] Int. Cl.⁶ ............................................. G01N 17/00
[52] U.S. Cl. ................................. 73/865.9; 73/150 R
[58] Field of Search ................................. 73/104, 865.9, 73/150 R, 827, 842, 845

[56] References Cited

U.S. PATENT DOCUMENTS 4,510,798  4/1985  Prussin et al. ........................ 73/150 R
5,344,236  9/1994  Fishman .

*Primary Examiner*—Robert Raevis
*Attorney, Agent, or Firm*—Majestic, Parson, Siebert & Hsue

[57] ABSTRACT

A method of identifying a weakest interface where delamination is most likely to occur in a multi-layer dielectric film stack formed on a semiconductor wafer includes scribing processed layers including the multi-layer dielectric film stack with an applied force of a selected and constant magnitude, measuring the depth of a cavity formed in the processed layers by such scribing, and identifying the weakest interface by comparing the measured depth against the known depths of the interfaces between adjacent layers of the multi-layer dielectric film stack.

13 Claims, 3 Drawing Sheets

METHOD OF IDENTIFYING A WEAKEST INTERFACE WHERE DELAMINATION IS MOST LIKELY TO OCCUR IN A MULTI-LAYER DIELECTRIC FILM STACK

BACKGROUND OF THE INVENTION

This invention relates in general to semiconductor device failure analysis methods and in particular, to a method of identifying a weakest interface where delamination is most likely to occur in a multi-layer dielectric film stack.

Multi-layer dielectric film stacks consisting of, for example, a spin-on glass ("SOG") layer sandwiched between plasma-enhanced chemical vapor deposition ("PECVD") oxide layers are commonly used as intermetal dielectric ("IMD") stacks in integrated circuit ("IC") semiconductor manufacturing. One problem with non-etch-backed PECVD-Ox/SOG/PECVD-Ox stacks, particularly for large semiconductor die, is delamination of the IMD stack at the SOG layer.

As an example, multi-level metallization is important for the performance and circuit density of Application Specific Integrated Circuits ("ASICs"). In ASIC designs, large dies having extensive areas without metallization are not uncommon, and these areas are known to delaminate when non-etchbacked IMD stacks are used. In order to study delamination mechanisms in such multi-layer IMD stacks, it is useful to know the weakest interface where delamination is most likely to occur in such multi-layer IMD stacks.

OBJECTS AND SUMMARY OF THE INVENTION

Accordingly, one object of the present invention is a simple, reliable test for determining the weakest interface where delamination is most likely to occur in a non-etchbacked IMD stack.

This and additional objects are accomplished by the various aspects of the present invention, wherein briefly stated, one aspect of the present invention is a method of identifying a weakest interface where delamination is most likely to occur between adjacent layers in a multi-layer dielectric film stack formed within processed layers of a semiconductor wafer, comprising the steps of: contacting a top surface of the processed layers with a pointed instrument applied with a force such that a cavity having a depth is formed in the processed layers by the pointed instrument; measuring the depth of the cavity formed in the processed layers by the pointed instrument applied with the force; and identifying the weakest interface where delamination is most likely to occur in the multi-layer dielectric film stack from the measured depth of the cavity formed in the processed layers by the pointed instrument applied with the force.

In the preferred embodiment of the method, the contacting step comprises the step of repetitively scribing the top surface of the processed layers with a pointed instrument applied with a force such that a plurality of cavities are formed in the processed layers by the pointed instrument; the measuring step comprises the step of measuring the respective depths of at least two of the plurality of cavities formed in the processed layers by the pointed instrument applied with the force; and the identifying step comprises the step of comparing the measured depths of the at least two of the plurality of cavities formed in the processed layers against a plurality of expected depths below the top surface of the processed layers, wherein the plurality of expected depths respectively correspond to a plurality of interfaces individually occurring between adjacent layers in the multi-layer dielectric film stack.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
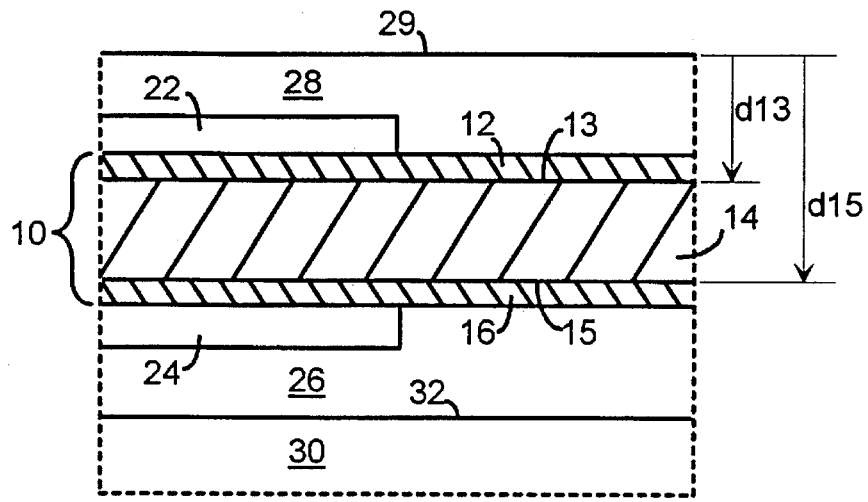
FIG. 1 illustrates, as an example, a partial cross-sectional view of a multi-layer dielectric film stack formed within processed layers of a semiconductor wafer.

FIG. 1 illustrates, as a simplified example, a partial cross-sectional view of a semiconductor wafer including a silicon substrate 30 and a number of processed layers formed on a top surface 32 of the silicon substrate 30. The processed layers include a first and second level of metallization, 24 and 22, respectively, a dielectric layer 26 electrically isolating the first level of metallization 24 from the silicon substrate 30, a multi-layer dielectric film stack 10 electrically isolating the first and second levels of metallization, 24 and 22, respectively, from each other, and a passivation layer 28 formed as a top layer of the processed layers.

The multi-layer dielectric film stack 10 includes a cap-layer PECVD oxide 12, a SOG layer 14, and a base-layer PECVD oxide 16. The abutting surfaces of the cap-layer PECVD oxide 12 and the SOG layer 14 define a first interface 13, and the abutting surfaces of the SOG layer 14 and the base-layer PECVD oxide 16 define a second interface 15. The first interface 13 is at a depth "d13" from a top surface 29 of the passivation layer 28, and the second interface 15 is at a depth "d15" from the top surface 29 of the passivation layer 28. Since the passivation layer 28 is the top layer of the processed layers, the top surface 29 of the passivation layer 28 is also the top surface of the processed layers.

Figure 2A:
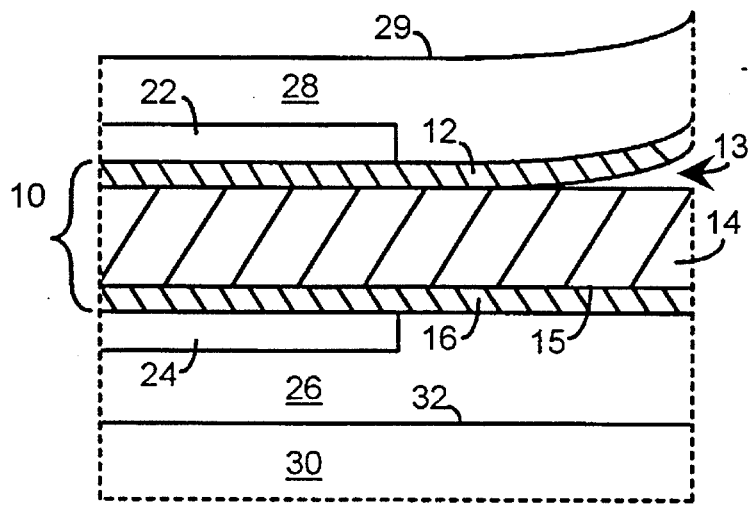
FIGS. 2A and 2B illustrate, as examples, partial cross-sectional views of delaminated interfaces occurring between different adjacent layers in a multilayer dielectric film stack formed within processed layers of a semiconductor wafer such as depicted in FIG. 1.
Figure 2B:
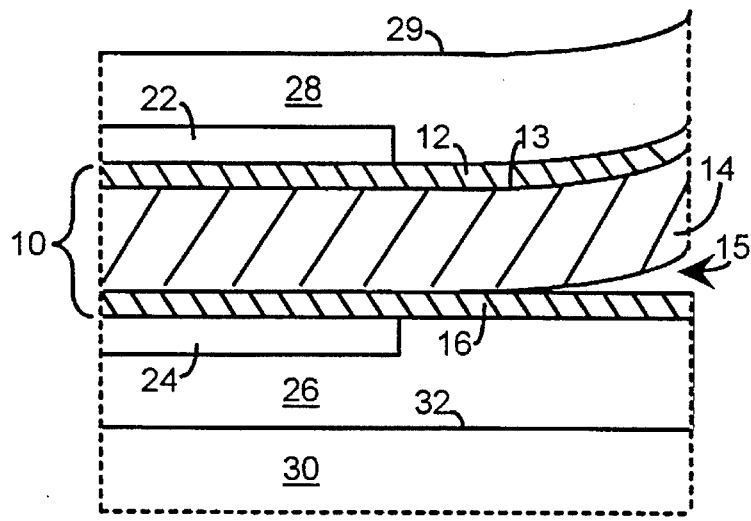

FIGS. 2A and 2B respectively illustrate, as examples, partial cross-sectional views of the processed layers depicted in FIG. 1 with delamination occurring at the first and second interfaces, 13 and 15. In particular, FIG. 2A illustrates delamination occurring at the first interface 13 by the cap-layer PECVD oxide 12 (and all other layers above it) partially "lifting off" the SOG layer 14, and FIG. 2B illustrates delamination occurring at the second interface 15 by the SOG layer 14 (and all other layers above it) partially "lifting off" the base-layer PECVD oxide 16. If additional layers beyond those depicted in FIGS. 2A and 2B are formed in the multi-layer dielectric film stack 10, then additional interfaces would be defined in the multi-layer dielectric film stack giving rise to the possibility of delamination occurring at those additional interfaces. If the dielectric layer 26 is also a multi-layer dielectric film stack, then additional interfaces would be defined therein giving rise to delamination potentially occurring at those additional interfaces.

Delamination is generally believed to occur at a weakest interface between adjacent layers in the multi-layer dielectric film stack 10. Due to the composition of and/or processing techniques employed in forming the processed layers, different interfaces in the multi-layer dielectric film stack 10, such as for example, interfaces 13 and 15, may result in being the weakest interface.

In order to study delamination mechanisms in IMD stacks such as the multi-layer dielectric film stack 10 depicted in FIG. 1, it is useful to determine at which interface delamination has occurred or is likely to occur in the IMD stack. A conventional technique for making such a determination is to prepare and view a cross-section of a number of such delaminated IMD stacks under a high powered microscope such as, for example, a scanning electron microscope ("SEM"). One problem with such a technique, however, is that delamination generally occurs after the integrated circuit has been packaged. To analyze such packaged ICs, the packaging must first be removed without further damaging the encased IC. This is especially cumbersome for plastic packaged parts. Additionally, such SEM techniques are cumbersome and time consuming. Therefore, a simpler technique providing reliable results is desirable.

In particular, it would be desirable to determine the weakest interface where delamination is most likely to occur in a multi-layer dielectric film stack before the IC is packaged. It would especially be desirable to make such determination at the wafer level.

A repeatable destructive test developed for this purpose includes scribing the top surface 29 of the processed layers using, for example, a scribing system such as a SUSS HR 100A manufactured by Karl Suss. In doing this, a diamond scribe formed, for example, as a pointed instrument, preferably contacts a top surface of the processed layers with an applied force of constant magnitude. Experiments refining the technique of the present invention have demonstrated that an applied force of approximately 1.2 Newtons provides effective results, and applied forces between 1.0 and 1.4 Newtons are expected to provide similarly effective results. To apply a measured force of approximately 1.2 Newtons using the SUSS HR 100A, a weight on a scriber adjustment bar of the SUSS HR 100A was set to approximately 1.0 cm from the diamond scribe of the SUSS HR 100A. A tool angle of 32° from vertical and a "toe" angle of 3° for the diamond scribe was used.

Figure 3A:
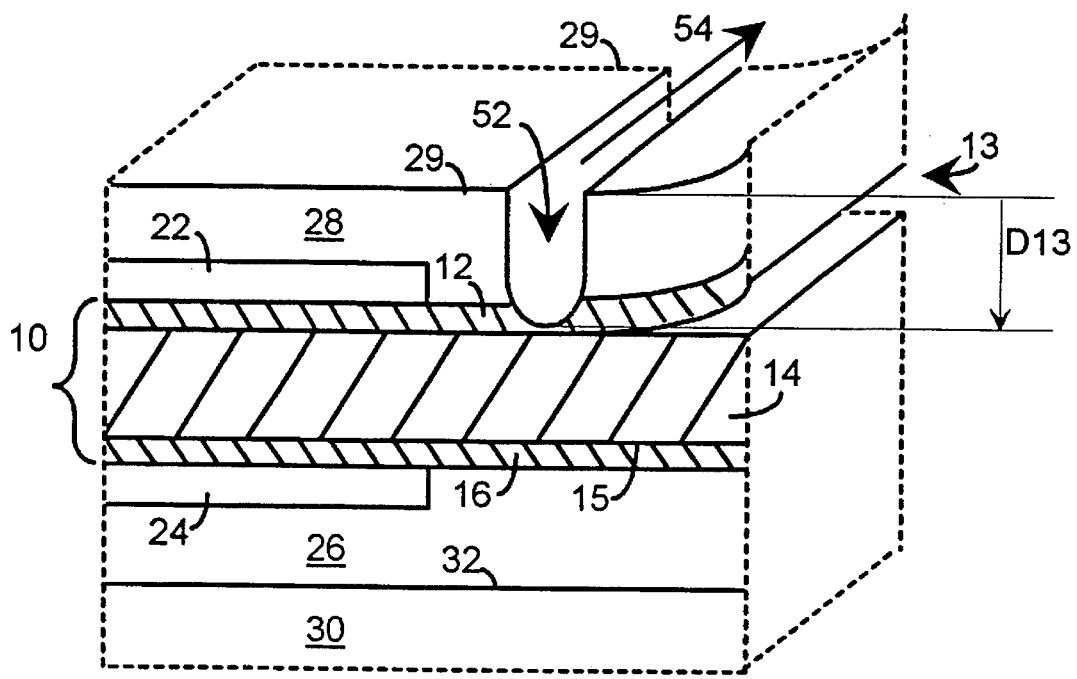
FIGS. 3A and 3B illustrate, as examples, partial cross-sectional views of scribe lines formed in the processed layers of two different semiconductor wafers, and delaminations respectively formed in the two different multi-layer dielectric film stacks as a result of such scribe lines.
Figure 3B:
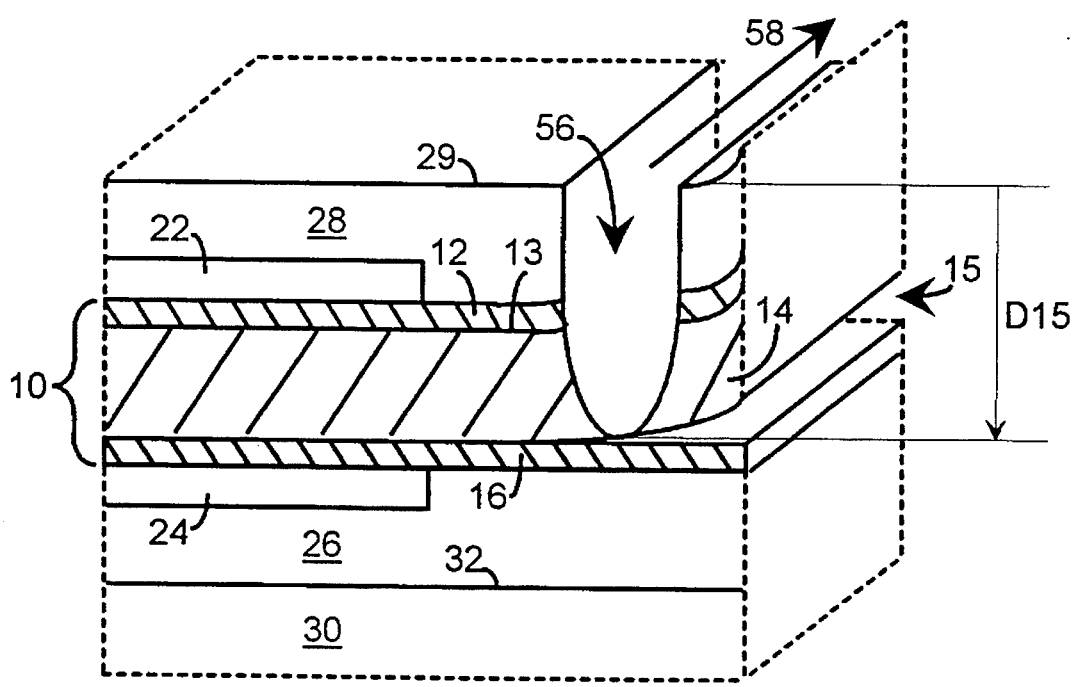

The scribe line takes the shape of an extended cavity or groove formed in the processed layers of the semiconductor wafer. The measured depth of the cavity at any cross-section transverse to the direction of the scribe line has been found to be indicative of which interface has delaminated as a result of such scribe line and in particular, which interface is weakest and most likely to delaminate in field usage. For example, FIG. 3A illustrates a scribe line 54 having an extended cavity 52 formed in processed layers of a semiconductor wafer wherein the interface 13 defined by abutting surfaces of the cap-layer PECVD oxide 12 and the SOG layer 14 has delaminated as a result of such scribe line 54. A depth D13 of the extended cavity 52 is shown in FIG. 3A to extend down towards the original depth d13 (FIG. 1) of the interface 13. Likewise, FIG. 3B illustrates a scribe line 58 having an extended cavity 56 formed in processed layers of a semiconductor wafer wherein the interface 15 defined by abutting surfaces of the SOG layer 14 and the base-layer PECVD oxide 16 has delaminated. A depth D15 of the extended cavity 56 is shown in FIG. 3B to extend beyond the depth d13 (FIG. 1) of the interface 13, and down towards the original depth d15 (FIG. 1) of the interface 15.

Accordingly, by scribing the top surfaces of processed layers of semiconductor wafers with an applied force between approximately 1.0 to 1.4 Newtons, the resulting depths of the extended cavities or grooves, as measured from the top surface, are indicative of which interface in the multi-layer dielectric film stack has delaminated as a result of such scribing and in particular, which interface is weakest and most likely to delaminate in field usage. In particular, as shown in FIG. 3A and verified by experimentation refining the techniques of the present invention, if the measured depth (e.g., D13) of the resulting cavity (e.g., 52) is approximately the known depth (e.g., d13) of a first interface 13, then the delaminated interface is identified as the first interface 13. On the other hand, as shown in FIG. 3B and verified by experimentation refining the techniques of the present invention, if the measured depth (e.g., D15) of the resulting cavity (e.g., 56) is approximately the known depth (e.g., d15) of a second interface 15, then the delaminated interface is identified as the second interface 15. Although not shown, delamination of additional layers beyond those depicted in FIGS. 3A and 3B, may also be identified by such scribing technique. For example, if the measured depth of the resulting cavity is approximately that of a third interface, then the delaminated interface in such case would be identified as the third interface.

The depth of the extended cavity resulting from scribing the processed layers of the semiconductor wafer with an applied force is measured, for example, by a Tencor AlphaStep 250 system. The depths for the non-delaminated interfaces of the multi-layer dielectric film stack 10 can be determined, for example, from process measurements and/or calculations, or measured from a known good processed wafer (i.e., not having any delaminated layers) by preparing and viewing a cross-section of the wafer under a high powered microscope such as, for example, a scanning electron microscope ("SEM").

Figure 4:
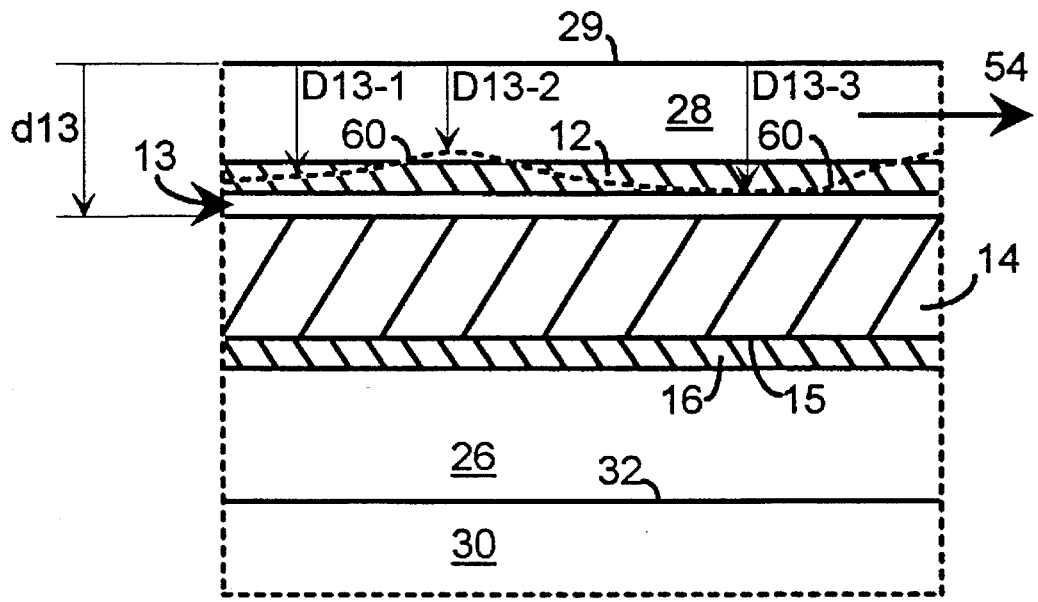
FIG. 4 illustrates, as an example, a partial transverse cross-sectional view of the scribe line formed in the processed layers of the semiconductor wafer having the delaminated multi-layer dielectric film stack depicted in FIG. 3A.

FIG. 4 illustrates, as an example, a partial transverse cross-sectional view of the processed layers of the semiconductor wafer having the scribe line and delaminated multi-layer dielectric film stack depicted in FIG. 3A. Depths D13-1, D13-2, and D13-3 measured at different points along the bottom 60 of the extended cavity 52 are shown, in an exaggerated fashion, to be of different values. As a refinement to the previously described technique, statistical analysis of such measured points, in lieu of using only a single measurement taken at one point, may be used and compared against the known depths of the interfaces in the same fashion as previously described in reference to the single measured depth used to identify a delaminated interface in a multi-layer dielectric film stack.

Figure 5:
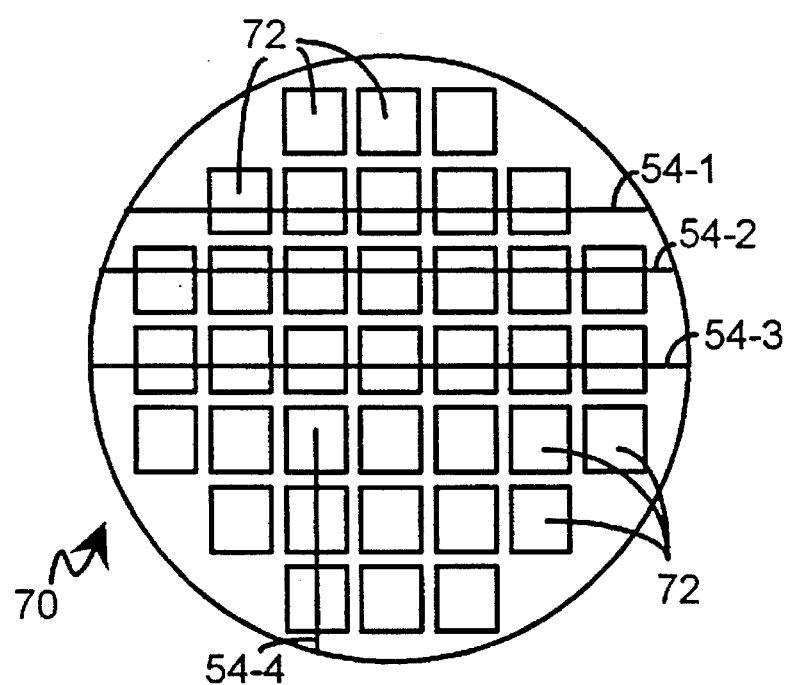
FIG. 5 illustrates, as an example, a top plan view of a semiconductor wafer having a plurality of scribe lines formed on its top surface.

FIG. 5 illustrates, as an example, a top plan view of a semiconductor wafer 70 having a plurality of scribe lines, 54-1 to 54-4, formed on its top surface. The semiconductor wafer 70 includes a plurality of integrated circuit die 72 formed on its top surface. Normally, a scriber system such as the SUSS HR 100A is used to break up the semiconductor wafer 70 into a plurality of individual integrated die, by scribing lines between the plurality of integrated circuit die 72 and breaking the wafer along the scribe lines. For the purposes of the present invention, however, the scriber system is used to precisely "scratch" processed layers over the plurality of integrated circuit die 72 with a pointed instrument, such as the diamond scriber of the scribing system, applied with a constant force of a preselected and fixed magnitude. A scriber system such as the SUSS HR 100A scriber system is preferred for such a function, because it is readily adapted to providing such an applied force.

As still another refinement to the previously described technique, a plurality of scribe lines such as shown for example in as scribe lines 54-1 to 54-4 in FIG. 5 may be formed on the processed layers of the semiconductor wafer 70 in lieu of only one such scribe line as previously described. Depth measurements may then be taken along each of the scribe lines 54-1 to 54-4, and an average of the measured points may be computed and compared against the known depths of the interfaces in the same fashion as previously described in reference to the single measured depth used to identify a delaminated interface in a multi-layer dielectric film stack.

Although the various aspects of the present invention have been described with respect to a preferred embodiment, it will be understood that the invention is entitled to full protection within the full scope of the appended claims.

What is claimed is:

1. A method of identifying a weakest interface where delamination is most likely to occur between adjacent layers in a multi-layer dielectric film stack formed within processed layers of a semiconductor wafer, comprising the steps of:

contacting a top surface of said processed layers with a pointed instrument applied with a force such that a cavity having a depth is formed in said processed layers by said pointed instrument;

measuring the depth of said cavity; and identifying the weakest interface where delamination is most likely to occur from the measured depth of said cavity.

2. The method as recited in claim 1, wherein said identifying step comprises the step of comparing the measured depth of said cavity against an expected depth below said top surface of said processed layers of an interface occurring between adjacent layers in said multi-layer dielectric film stack.

3. The method as recited in claim 1, wherein said contacting step comprises the step of scribing said top surface of said processed layers with a pointed instrument applied with a force such that a scribe line having a cavity is formed in said processed layers by said pointed instrument.

4. The method as recited in claim 3, wherein said measuring step comprises the step of measuring the depth of said cavity at a plurality of points along said scribe line, and said identifying step comprises the step of identifying the weakest interface from a statistical analysis of the measured depths taken along said scribe line.

5. The method as recited in claim 4, wherein said identifying step comprises the step of comparing the measured depths taken along said scribe line against an expected depth below said top surface of said processed layers of an interface occurring between adjacent layers in said multi-layer dielectric film stack.

6. The method as recited in claim 5, wherein said identifying step comprises the step of comparing the measured depths taken along said scribe line against a plurality of expected depths below said top surface of processed layers, wherein said plurality of expected depths respectively correspond to a plurality of interfaces individually occurring between adjacent layers in said multi-layer dielectric film stack.

7. The method as recited in claim 1, wherein said contacting step comprises the step of scribing said top surface of said processed layers with a pointed instrument applied with a force between 1.1 and 1.4 Newtons such that a scribe line having a cavity is formed in said processed layers by said pointed instrument.

8. A method of identifying a weakest interface where delamination is most likely to occur between adjacent layers in a multi-layer dielectric film stack formed within processed layers of a semiconductor wafer, comprising the steps of:

repetitively contacting a top surface of said processed layers with a pointed instrument applied with a force such that a plurality of cavities individually having a depth are formed in said processed layers by said pointed instrument;

measuring the respective depths of at least two of said plurality of cavities formed in said processed layers by said pointed instrument applied with said force; and identifying said weakest interface where delamination is most likely to occur in said multi-layer dielectric film stack from a statistical analysis of the measured depths of the at least two of said plurality of cavities formed in said processed layers by said pointed instrument applied with said force.

9. The method as recited in claim 8, wherein said identifying step comprises the step of comparing the measured depths of the at least two of said plurality of cavities formed in said processed layers against an expected depth below said top surface of said processed layers of an interface occurring between adjacent layers in said multi-layer dielectric film stack.

10. The method as recited in claim 8, wherein said repetitively contacting step comprises the step of repetitively scribing said top surface of said processed layers with a pointed instrument applied with a force such that a plurality of scribe lines having corresponding cavities and depths are formed in said processed layers by said pointed instrument.

11. The method as recited in claim 10, wherein said identifying step comprises the step of comparing the measured depths of the at least two of said plurality of scribe lines formed in said processed layers against an expected depth below said top surface of said processed layers of an interface occurring between adjacent layers in said multi-layer dielectric film stack.

12. The method as recited in claim 11, wherein said identifying step comprises the step of comparing the measured depths of the at least two of said plurality of scribe lines formed in said processed layers against a plurality of expected depths below said top surface of said processed layers, wherein said plurality of expected depths respectively correspond to a plurality of interfaces individually occurring between adjacent layers in said multi-layer dielectric film stack.

13. The method as recited in claim 8, wherein said repetitively contacting step comprises the step of repetitively scribing said top surface of said processed layers with a pointed instrument applied with a force between 1.1 and 1.4 Newtons such that a plurality of scribe lines having cavities are formed in said processed layers by said pointed instrument.

* * * * *